United States Patent
Polosky et al.

(10) Patent No.: US 12,185,907 B2
(45) Date of Patent: *Jan. 7, 2025

(54) SURGICAL INSTRUMENTS AND SYSTEMS AND METHODS FOR DETERMINING CONDITION INFORMATION THEREOF

(71) Applicant: Intuitive Surgical Operations, Inc., Sunnyvale, CA (US)

(72) Inventors: Quentin F. Polosky, Santa Clara, CA (US); Diana C. W. Friedman, Burlingame, CA (US); Mathew D. Clopp, Santa Clara, CA (US); Yves Lacroix, San Jose, CA (US); John A Barton, San Jose, CA (US); Dean A. Mansour, Redwood City, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/109,562

(22) Filed: Feb. 14, 2023

(65) Prior Publication Data
US 2023/0270317 A1     Aug. 31, 2023

Related U.S. Application Data

(63) Continuation of application No. 16/886,391, filed on May 28, 2020, now Pat. No. 11,602,258.
(Continued)

(51) Int. Cl.
*A61B 1/00*     (2006.01)
*A61B 17/3201*     (2006.01)
(Continued)

(52) U.S. Cl.
CPC ...... *A61B 1/00029* (2013.01); *A61B 1/00016* (2013.01); *A61B 1/0002* (2013.01);
(Continued)

(58) Field of Classification Search
CPC ............ A61B 1/00029; A61B 1/00016; A61B 1/0002; A61B 1/00055; A61B 1/00057;
(Continued)

(56) References Cited

U.S. PATENT DOCUMENTS

| | | | |
|---|---|---|---|
| 11,602,258 B2 | 3/2023 | Polosky et al. | |
| 2005/0148819 A1* | 7/2005 | Noguchi | A61L 2/24 600/101 |

(Continued)

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Andrew M Tecco
*Assistant Examiner* — Nicholas E Igbokwe

(57) ABSTRACT

An exemplary system includes a memory storing instructions and a processor communicatively coupled to the memory. The processor is configured to execute the instructions to receive, from a sensor of a surgical instrument, environmental condition information associated with the surgical instrument and detected by the sensor while the surgical instrument is disconnected from an external power source, the surgical instrument including circuitry configured to be powered and operate only while the surgical instrument is connected to the external power source, determine, based on the environmental condition information, an operational condition of the surgical instrument, and provide a notification indicating the determined operational condition of the surgical instrument.

17 Claims, 11 Drawing Sheets

Related U.S. Application Data

(60) Provisional application No. 62/855,496, filed on May 31, 2019.

(51) Int. Cl.
*A61B 18/14* (2006.01)
*A61B 17/00* (2006.01)
*A61B 18/00* (2006.01)

(52) U.S. Cl.
CPC ...... *A61B 1/00055* (2013.01); *A61B 1/00057* (2013.01); *A61B 1/00059* (2013.01); *A61B 1/00149* (2013.01); *A61B 17/3201* (2013.01); *A61B 18/14* (2013.01); *A61B 2017/00119* (2013.01); *A61B 2017/00221* (2013.01); *A61B 2017/00734* (2013.01); *A61B 2018/00595* (2013.01); *A61B 2560/0242* (2013.01); *A61B 2560/0276* (2013.01)

(58) Field of Classification Search
CPC ............ A61B 1/00059; A61B 1/00149; A61B 17/3201; A61B 18/14; A61B 2017/00119; A61B 2017/00221; A61B 2017/00734; A61B 2018/00595; A61B 2560/0242; A61B 2560/0276
See application file for complete search history.

(56) References Cited

U.S. PATENT DOCUMENTS

| | | | | |
|---|---|---|---|---|
| 2008/0281254 | A1* | 11/2008 | Humayun | A61B 90/98 604/22 |
| 2008/0283576 | A1* | 11/2008 | Boyden | A61B 17/068 227/180.1 |
| 2010/0168562 | A1* | 7/2010 | Zhao | A61B 34/30 600/426 |
| 2013/0214025 | A1* | 8/2013 | Zemlok | A61B 17/07207 227/175.1 |
| 2014/0207124 | A1* | 7/2014 | Aldridge | A61B 18/1445 606/1 |
| 2016/0287349 | A1* | 10/2016 | Bzostek | H04B 5/0037 |
| 2018/0353061 | A1* | 12/2018 | Tanaka | A61B 1/05 |
| 2019/0201041 | A1* | 7/2019 | Kimball | A61B 34/30 |
| 2019/0201084 | A1* | 7/2019 | Shelton, IV | A61B 18/14 |

* cited by examiner

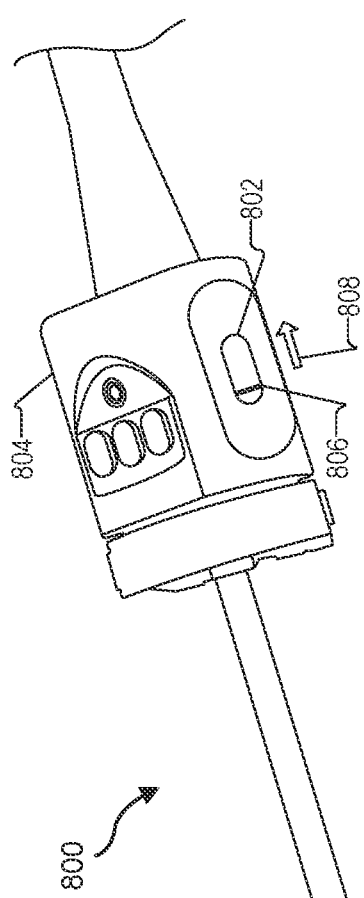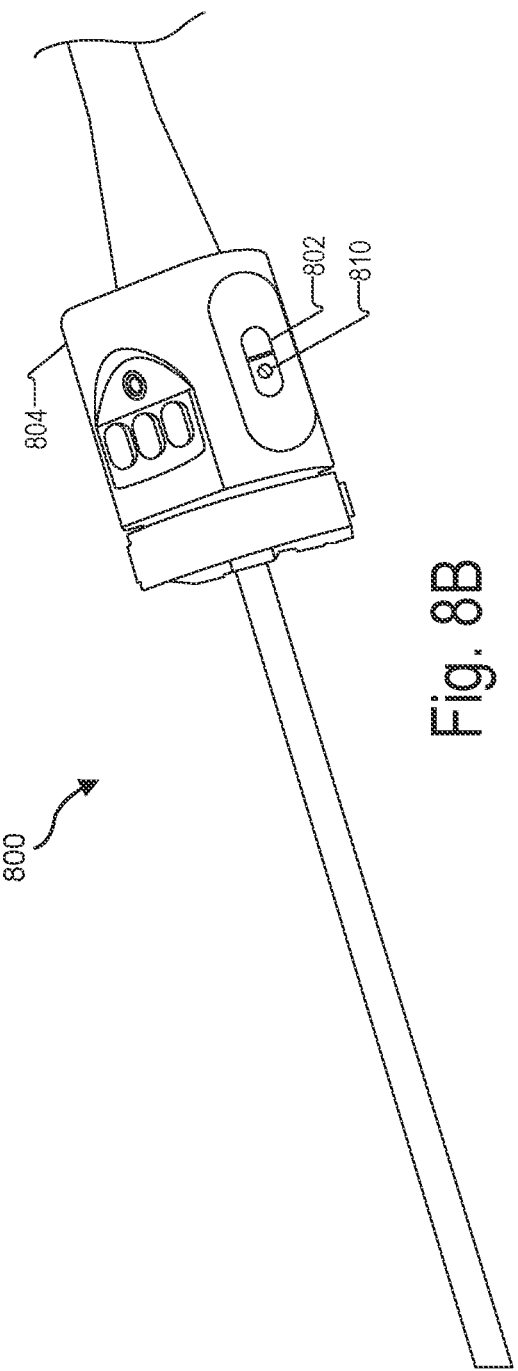

SURGICAL INSTRUMENTS AND SYSTEMS AND METHODS FOR DETERMINING CONDITION INFORMATION THEREOF

RELATED APPLICATIONS

This application is a continuation application of U.S. patent application Ser. No. 16/886,391, filed May 28, 2020, which claims priority to and the benefit of U.S. Provisional Patent Application No. 62/855,496, filed May 31, 2019, each of which is hereby incorporated by reference in its entirety.

BACKGROUND INFORMATION

A computer-assisted surgical system allows a surgeon to control robotically-manipulated surgical instruments to perform a surgical procedure on a patient. For a minimally-invasive surgery, for example, robotically-manipulated surgical instruments are inserted into a patient through one or more cannulas. The surgical instruments typically include an endoscope that captures images of a surgical area and one or more surgical tools that are robotically manipulated by the computer-assisted surgical system to perform a surgical procedure. A surgeon views the endoscopic images of the surgical area and uses master controls of the computer-assisted surgical system to control movement of the surgical instruments to perform the surgical procedure.

During the surgical procedure, the surgical instruments are attached to manipulator arms of a surgical instrument manipulating system included as part of the computer-assisted surgical system. After the surgical procedure, the surgical instruments are typically removed from the manipulator arms and are subjected to one or more sterilization procedures to prepare the surgical instruments to be used again (e.g., in a subsequent surgical procedure with a different patient). However, prior to the surgical procedure, during the surgical procedure, and/or after the surgical procedure, a surgical instrument may be subjected to one or more events or conditions that may prevent the surgical instrument from operating properly. For example, an endoscope may undergo a sterilization procedure after the surgical procedure that results in moisture entering a housing of the endoscope, which presence of moisture may result in degraded operation of the endoscope. Additionally or alternatively, a user may drop the endoscope before, during, and/or after the surgical procedure, which may result in damage to one or more lenses of the endoscope. The surgeon and/or other individuals may not be aware that such events or conditions have occurred, when they occurred, or how to prevent them from occurring again, which may result in wasted time diagnosing a faulty surgical instrument, unsafe conditions during a surgical procedure (e.g., if the surgical instrument was not sterilized properly), and/or inefficiently performed surgical procedures.

SUMMARY

An exemplary surgical instrument comprises: circuitry configured to be powered and operate only while the surgical instrument is connected to an external power source; a sensor configured to detect environmental condition information associated with the surgical instrument while the surgical instrument is disconnected from the external power source; and a memory configured to store the environmental condition information detected by the sensor while the surgical instrument is disconnected from the external power source.

An exemplary system comprises a memory storing instructions, and a processor communicatively coupled to the memory and configured to execute the instructions to: receive, from a sensor of a surgical instrument, environmental condition information associated with the surgical instrument and detected by the sensor while the surgical instrument is disconnected from an external power source, the surgical instrument including circuitry configured to be powered and operate only while the surgical instrument is connected to the external power source; determine, based on the environmental condition information, an operating condition of the surgical instrument; and provide a notification indicating the determined operational condition of the surgical instrument.

An exemplary method comprises receiving, by an instrument condition detection system from a sensor of a surgical instrument, environmental condition information associated with the surgical instrument and detected by the sensor while the surgical instrument is disconnected from an external power source, the surgical instrument including circuitry configured to be powered and operate only while the surgical instrument is connected to the external power source; determining, by the instrument condition detection system based on the environmental condition information, an operating condition of the surgical instrument; and providing, by the instrument condition detection system, a notification indicating the determined operational condition.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 8A and 8B illustrate an exemplary configuration of a surgical instrument according to principles described herein.

DETAILED DESCRIPTION

Surgical instruments and systems and methods for determining condition information thereof are described herein. As will be described in more detail below, an exemplary surgical instrument comprises circuitry configured to be powered and operate only while the surgical instrument is connected to an external power source, a sensor configured to detect environmental condition information associated with the surgical instrument while the surgical instrument is disconnected from the external power source, a memory configured to store the environmental condition information detected by the sensor while the surgical instrument is disconnected from the external power source. In certain examples, surgical instruments such as those described herein may further include an internal power source disposed within the housing and configured to provide operating power to the sensor and the memory while the surgical instrument is disconnected from the external power source.

Various advantages and benefits are associated with the surgical instruments, systems, and methods described herein. For example, systems and methods such as those described herein facilitate monitoring the condition of a surgical instrument during an entire life cycle of the surgical instrument (e.g., during transport from a manufacturer, prior to being removed from manufacturer packaging, during a surgical procedure, after a surgical procedure, during a sterilization procedure, during reuse of the surgical instrument in an additional surgical procedure, etc.). In addition, systems and methods such as those described herein are configured to facilitate providing notifications and/or training to users on best practices associated with caring for and/or using surgical instruments. Further, the systems and methods described herein may facilitate tracking and/or managing surgical instrument inventory at a facility (e.g., a hospital). These and other benefits that may be realized by the systems and methods described herein will be evident from the disclosure that follows.

In certain examples, the exemplary surgical instruments, methods, and systems described herein may operate as part of or used in conjunction with a computer-assisted surgical system. Accordingly, an exemplary computer-assisted surgical system will now be described with reference to FIG. 1. The described exemplary computer-assisted surgical system is illustrative and not limiting. Surgical instruments, systems, and methods such as those described herein may operate as part of or in conjunction with the described computer-assisted surgical system and/or any other suitable computer-assisted surgical system.

Figure 1:
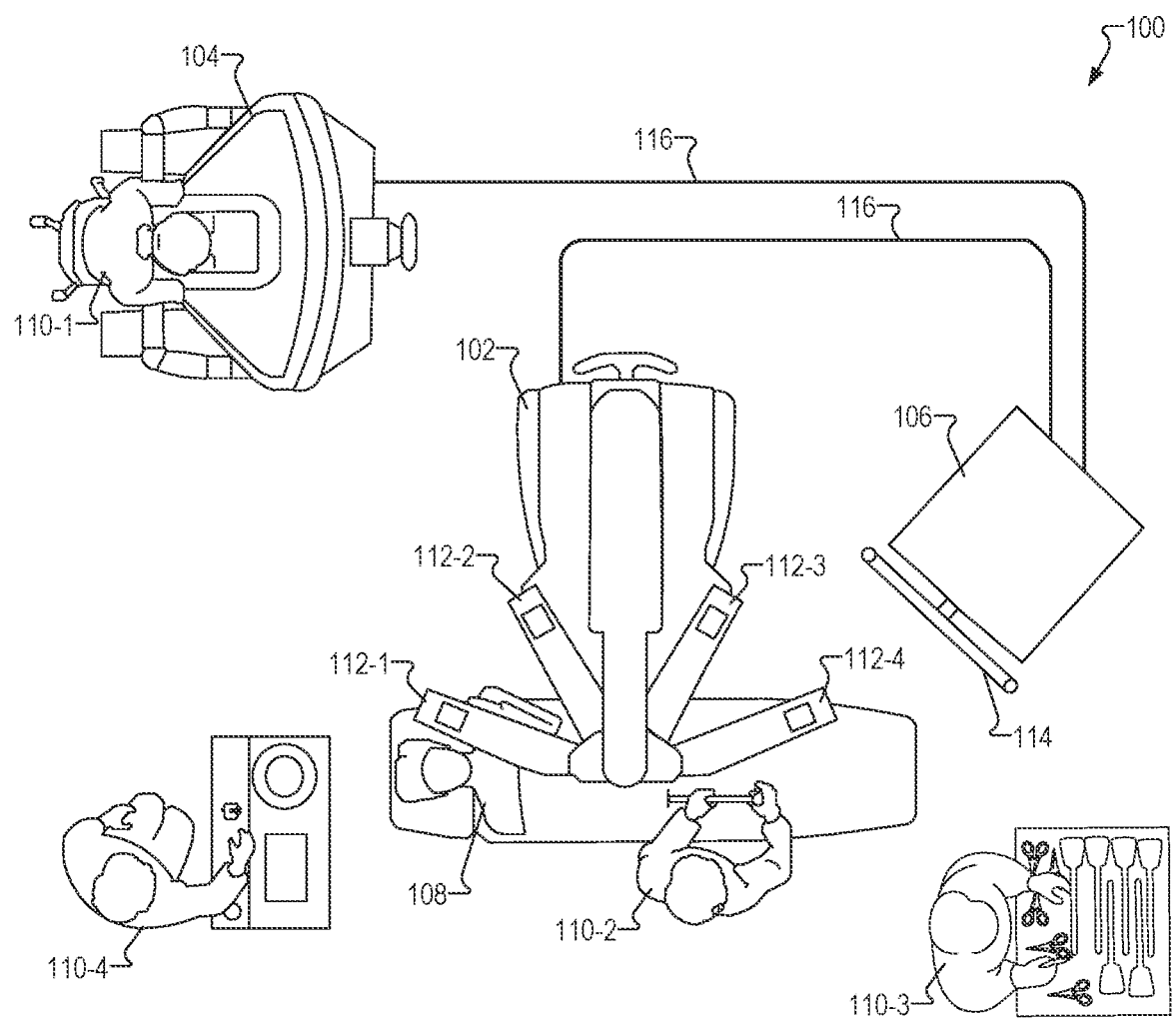
FIG. 1 illustrates an exemplary computer-assisted surgical system according to principles described herein.

FIG. 1 illustrates an exemplary computer-assisted surgical system 100 ("surgical system 100"). As shown, surgical system 100 may include a surgical instrument manipulating system 102 ("manipulating system 102"), a user control system 104, and an auxiliary system 106 communicatively coupled one to another.

Surgical system 100 may be utilized by a surgical team to perform a computer-assisted surgical procedure on a patient 108. As shown, the surgical team may include a surgeon 110-1, an assistant 110-2, a nurse 110-3, and an anesthesiologist 110-4, all of whom may be collectively referred to as "surgical team members 110." Additional or alternative surgical team members may be present during a surgical session as may serve a particular implementation.

While FIG. 1 illustrates an ongoing minimally invasive surgical procedure, surgical system 100 may similarly be used to perform open surgical procedures or other types of surgical procedures that may similarly benefit from the accuracy and convenience of surgical system 100. Additionally, it will be understood that the surgical session throughout which surgical system 100 may be employed may not only include an operative phase of a surgical procedure, as is illustrated in FIG. 1, but may also include preoperative, postoperative, and/or other suitable phases of the surgical procedure. A surgical procedure may include any procedure in which manual and/or instrumental techniques (e.g., teleoperated instrumental techniques) are used on a patient to investigate, diagnose, or treat a physical condition of the patient. Additionally, a surgical procedure may include any procedure that is not performed on a live patient, such as a calibration procedure, a simulated training procedure, and an experimental or research procedure.

As shown in FIG. 1, surgical instrument manipulating system 102 may include a plurality of manipulator arms 112 (e.g., manipulator arms 112-1 through 112-4) to which a plurality of surgical instruments (not shown) may be coupled. Each surgical instrument may be implemented by any suitable surgical tool (e.g., a tool having tissue-interaction functions), medical tool, monitoring instrument (e.g., an imaging device such as an endoscope), sensing instrument (e.g., a force-sensing surgical instrument), diagnostic instrument, or the like that may be used for a computer-assisted surgical procedure (e.g., by being at least partially inserted into patient 108 and manipulated to perform a computer-assisted surgical procedure on patient 108). In the example, shown in FIG. 1, manipulator arms 112 of manipulating system 102 are attached on a distal end of an overhead boom that extends horizontally. However, manipulator arms 112 may have other configurations in certain implementations. In addition, while manipulating system 102 is depicted and described herein as including four manipulator arms 112, it will be recognized that manipulating system 102 may include only a single manipulator arm 112 or any other number of manipulator arms as may serve a particular implementation.

Manipulator arms 112 and/or surgical instruments attached to manipulator arms 112 may include one or more displacement transducers, orientational sensors, and/or positional sensors (hereinafter "surgical system sensors") used to generate raw (e.g., uncorrected) kinematics information. One or more components of surgical system 100 may be configured to use the kinematics information to track (e.g., determine positions of) and/or control the surgical instruments.

In addition, manipulator arms 112 may each include or otherwise be associated with a plurality of motors that control movement of manipulator arms 112 and/or the surgical instruments attached thereto. For example, manipulator arm 112-1 may include or otherwise be associated with a first internal motor (not explicitly shown) configured to yaw manipulator arm 112-1 about a yaw axis. In like manner, manipulator arm 112-1 may be associated with a second internal motor (not explicitly shown) configured to drive and pitch manipulator arm 112-1 about a pitch axis. Likewise, manipulator arm 112-1 may be associated with a third internal motor (not explicitly shown) configured to slide manipulator arm 112-1 along insertion axis. Manipulator arms 112 may each include a drive train system driven by one or more of these motors in order to control the pivoting of manipulator arms 112 in any manner as may serve a particular implementation. As such, if a surgical instrument attached, for example, to manipulator arm 112-1 is to be mechanically moved, one or more of the motors coupled to the drive train may be energized to move manipulator arm 112-1.

Surgical instruments attached to manipulator arms 112 may each be positioned at a surgical space associated with a patient. A "surgical space" may, in certain examples, be entirely disposed within a patient and may include an area within the patient at or near where a surgical procedure is planned to be performed, is being performed, or has been performed. For example, for a minimally invasive surgical procedure being performed on tissue internal to a patient, the surgical space may include the tissue, anatomy underlying the tissue, as well as space around the tissue where, for example, surgical instruments being used to perform the surgical procedure are located. In other examples, a surgical space may be at least partially disposed external to the patient at or near where a surgical procedure is planned to be performed, is being performed, or has been performed on the patient. For instance, surgical system 100 may be used to perform an open surgical procedure such that part of the surgical space (e.g., tissue being operated on) is internal to the patient while another part of the surgical space (e.g., a space around the tissue where one or more surgical instruments may be disposed) is external to the patient. A surgical instrument may be referred to as being positioned or located at or within a surgical space when at least a portion of the surgical instrument (e.g., a distal portion of the surgical instrument) is located within the surgical space.

User control system 104 may be configured to facilitate control by surgeon 110-1 of manipulator arms 112 and surgical instruments attached to manipulator arms 112. For example, surgeon 110-1 may interact with user control system 104 to remotely move or manipulate manipulator arms 112 and the surgical instruments. To this end, user control system 104 may provide surgeon 110-1 with imagery (e.g., high-definition three-dimensional (3D) imagery) of a surgical space associated with patient 108 as captured by an imaging device. In certain examples, user control system 104 may include a stereoscopic image viewer having two displays where stereoscopic images (e.g., 3D images) of a surgical space associated with patient 108 and generated by a stereoscopic imaging system may be viewed by surgeon 110-1. Surgeon 110-1 may utilize the imagery to perform one or more procedures with one or more surgical instruments attached to manipulator arms 112.

To facilitate control of surgical instruments, user control system 104 may include a set of master controls (not shown). These master controls may be manipulated by surgeon 110-1 to control movement of surgical instruments (e.g., by utilizing robotic and/or teleoperation technology). The master controls may be configured to detect a wide variety of hand, wrist, and finger movements by surgeon 110-1. In this manner, surgeon 110-1 may intuitively perform a surgical procedure using one or more surgical instruments.

User control system 104 may further be configured to facilitate control by surgeon 110-1 of other components of surgical system 100. For example, surgeon 110-1 may interact with user control system 104 to change a configuration or operating mode of surgical system 100, to change a display mode of surgical system 100, to generate additional control signals used to control surgical instruments attached to manipulator arms 112, to facilitate switching control from one surgical instrument to another, to initiate display of a representation of an insertion trajectory, or to perform any other suitable operation. To this end, user control system 104 may also include one or more input devices (e.g., foot pedals, buttons, switches, etc.) configured to receive input from surgeon 110-1.

Auxiliary system 106 may include one or more computing devices configured to perform primary processing operations of surgical system 100. The one or more computing devices included in auxiliary system 106 may control and/or coordinate operations performed by various other components (e.g., manipulating system 102 and/or user control system 104) of surgical system 100. For example, a computing device included in user control system 104 may transmit instructions to manipulating system 102 by way of the one or more computing devices included in auxiliary system 106. As another example, auxiliary system 106 may receive, from manipulating system 102, and process image data representative of imagery captured by an imaging device attached to one of manipulator arms 112.

In some examples, auxiliary system 106 may be configured to present visual content to surgical team members 110 who may not have access to the images provided to surgeon 110-1 at user control system 104. To this end, auxiliary system 106 may include a display monitor 114 configured to display one or more user interfaces, such as images (e.g., 2D images) of the surgical space, information associated with patient 108 and/or the surgical procedure, and/or any other visual content as may serve a particular implementation. For example, display monitor 114 may display images of the surgical space together with additional content (e.g., representations of insertion trajectories, graphical content, contextual information, etc.) concurrently displayed with the images. In some embodiments, display monitor 114 is implemented by a touchscreen display with which surgical team members 110 may interact (e.g., byway of touch gestures) to provide user input to surgical system 100.

Manipulating system 102, user control system 104, and auxiliary system 106 may be communicatively coupled one to another in any suitable manner. For example, as shown in FIG. 1, manipulating system 102, user control system 104, and auxiliary system 106 may be communicatively coupled by way of control lines 116, which may represent any wired or wireless communication link as may serve a particular implementation. To this end, manipulating system 102, user control system 104, and auxiliary system 106 may each include one or more wired or wireless communication interfaces, such as one or more local area network interfaces, Wi-Fi network interfaces, cellular interfaces, etc.

During the life cycle of a surgical instrument configured to operate in conjunction system 100, the surgical instrument may experience certain conditions and/or events that may prevent the surgical instrument from operating properly. For example, while the surgical instrument is in packaging provided by a manufacturer and prior to being used in system 100, the surgical instrument may be dropped or otherwise damaged. Additionally or alternatively, after the surgical instrument is used in a surgical procedure through system 100, the surgical instrument may be subjected to a sterilization procedure (e.g., in an autoclave). However, the sterilization procedure may result in moisture entering the surgical instrument, which may cause the surgical instrument to be faulty in certain examples. Conditions and/or events such as these and others may occur without a user (e.g., surgeon 110-1, assistant 110-2, etc.) being aware that they have occurred and/or being aware that they may prevent the surgical instrument from operating properly. Accordingly, the systems and methods described herein are configured to facilitate detecting such conditions and/or events associated with a surgical instrument and providing a user and/or any other suitable entity with notifications regarding them.

Figure 2:
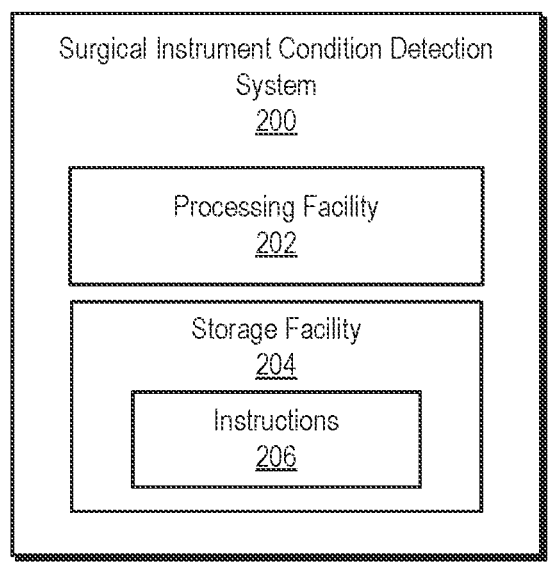
FIG. 2 illustrates an exemplary surgical instrument condition detection system according to principles described herein.

FIG. 2 illustrates an exemplary surgical instrument condition detection system 200 ("detection system 200") that may be implemented according to principles described herein. As shown, detection system 200 may include, without limitation, a processing facility 202 and a storage facility 204 selectively and communicatively coupled to one another. Facilities 202 and 204 may each include or be implemented by hardware and/or software components (e.g., processors, memories, communication interfaces, instructions stored in memory for execution by the processors, etc.). In some examples, facilities 202 and 204 may be implemented by a single device (e.g., a single surgical instrument). In certain alternate examples, facilities 202 and 204 may be distributed between multiple devices and/or multiple locations as may serve a particular implementation.

Storage facility 204 may maintain (e.g., store) executable data used by processing facility 202 to perform any of the operations described herein. For example, storage facility 204 may store instructions 206 that may be executed by processing facility 202 to perform any of the operations described herein. Instructions 206 may be implemented by any suitable application, software, code, and/or other executable data instance.

Storage facility 204 may also maintain any data received, generated, managed, used, and/or transmitted by processing facility 202. For example, storage facility 204 may maintain any suitable data associated with a condition of a surgical instrument and/or notifications that may be provided regarding the condition. As will be described in more detail below, such data may include environmental condition information. As used herein, "environmental condition information" refers to any information associated with conditions and/or events the surgical instrument has been subjected to during the life cycle of the surgical instrument. Environmental condition information may include, but is not limited to, information associated with temperatures the surgical instrument has experienced, humidity inside and/or outside of the surgical instrument, impacts that the surgical instrument has experienced (e.g., when dropped), a geographic location of a surgical instrument, and/or any other suitable condition and/or event.

Processing facility 202 may be configured to perform (e.g., execute instructions 206 stored in storage facility 204) various processing operations associated with detecting environmental condition information of a surgical instrument. For example, processing facility 202 may receive environmental condition information associated with a surgical instrument and detected by a sensor while the sensor uses operating power from an internal power source of the surgical instrument and while the surgical instrument is disconnected from an external power source. Based on the environmental condition information, processing facility 202 may determine an operational condition of the surgical instrument. Processing facility 202 may then provide a notification indicating the determined operational condition of the surgical instrument. These and other operations that may be performed by processing facility 202 are described herein.

Detection system 200 (e.g., processing facility 202) is configured to detect environmental condition information associated with a surgical instrument in order to determine what conditions the surgical instrument has been subjected to and whether the surgical instrument is in suitable condition for use (e.g., during a surgical procedure). To that end, detection system 200 is configured to leverage one or more sensors included as part of a surgical instrument to determine what conditions and/or events the surgical instrument has experienced. Exemplary sensors that may be included as part of a surgical instrument are described herein.

Detection system 200 may be configured to detect environmental condition information associated with any one of a plurality of different types of surgical instruments such as those described herein. For example, detection system 200 may be configured to detect environmental condition information associated with any suitable surgical tool (e.g., a tool having tissue-interaction functions), medical tool, monitoring instrument (e.g., an imaging device such as an endoscope), sensing instrument (e.g., a force-sensing surgical instrument), diagnostic instrument, or the like that may be used for a computer-assisted surgical procedure. Although the present disclosure describes detecting environmental condition information associated with surgical instruments that may be used in conjunction with a computer-assisted surgical system (e.g., system 100), it is understood that concepts such as those described herein may be implemented with any other type of instrument that may be usable with any other type of system.

Detection system 200 may be configured to control and/or interact with the various components of a surgical instrument in any suitable manner to facilitate performing the various operations described herein. Exemplary surgical instruments will now be described with reference to FIGS. 3 and 4.

Figure 3:
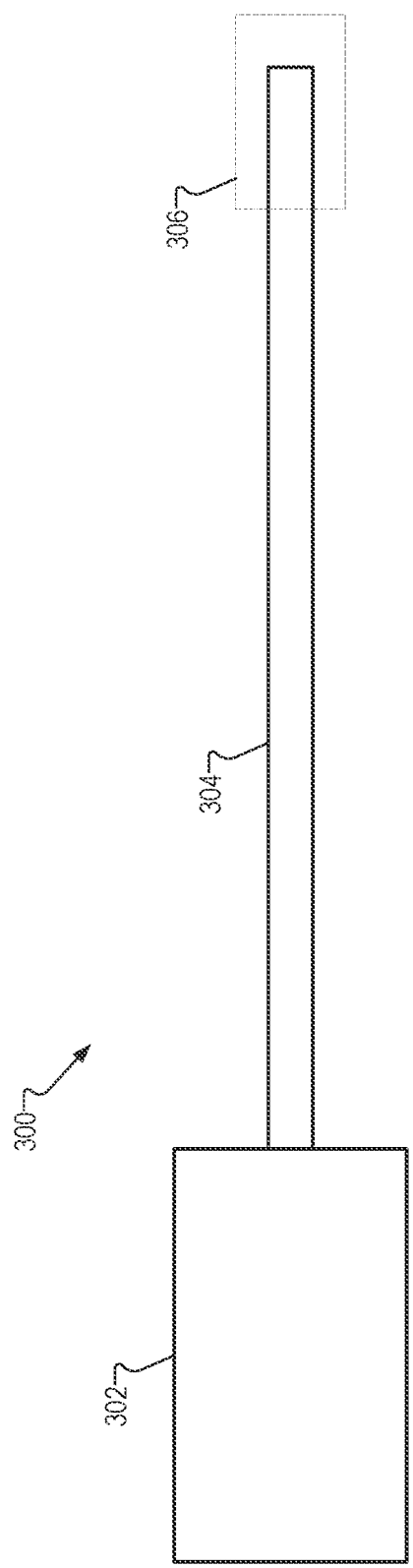
FIG. 3 illustrates an exemplary simplified schematic diagram of a surgical instrument according to principles described herein.

FIG. 3 shows an exemplary simplified schematic diagram of a surgical instrument 300 that may implement or may be used in conjunction with detection system 200. As shown in FIG. 3, surgical instrument 300 includes a housing 302, a shaft portion 304, and a distal end region 306. Housing 302 may be configured to connect to a manipulator arm (e.g., manipulator arm 112-1) of a computer assisted surgical system. Housing 302 is also configured to house one or more components associated with an intended function of surgical instrument 300 and/or associated with detecting environmental condition information. When surgical instrument 300 is connected to a manipulator arm, shaft portion 304 is configured to extend from the manipulator arm and into a surgical space (e.g., through a cannula). In certain examples, shaft portion 304 may also include one or more components associated with the function of surgical instrument 300 and/or associated with detecting environmental condition information. Exemplary components that may be included in or as part of housing 302 and/or shaft portion 304 are described herein.

In certain examples, surgical instrument 300 may also include a cord (not shown) configured to communicatively connect surgical instrument 300 to a component of system 100. For example, when surgical instrument 300 is implemented by an imaging device such as an endoscope, such a cord may communicatively connect surgical instrument 300 to auxiliary system 106 to facilitate surgical instrument 300 providing image data representative of imagery of a surgical space captured by surgical instrument 300.

Distal end region 306 of surgical instrument 300 may have any one of a plurality of different configurations depending on which type of surgical instrument is represented by surgical instrument 300. For example, when surgical instrument 300 is an imaging device (e.g., an endoscope), distal end region 306 may include one or more lenses, image sensors, and/or illuminators. In examples where surgical instrument 300 is an electrocautery device, distal end region 306 may include components suitable to generate an electric field used, for example, to cauterize tissue. In examples where surgical instrument 300 includes surgical scissors, distal end region 306 may include a pair of blades used to cut tissue. Distal end region 306 may have any other suitable configuration in certain implementations.

In certain examples, surgical instrument 300 may be a single use surgical instrument. Alternatively, surgical instrument 300 may be reusable as many times as may serve a particular implementation. In certain examples, surgical instrument 300 may be a short-term use surgical instrument (e.g., reusable up to 5 times) or a long-term use surgical instrument (e.g., reusable up to 200 times).

Figure 4:
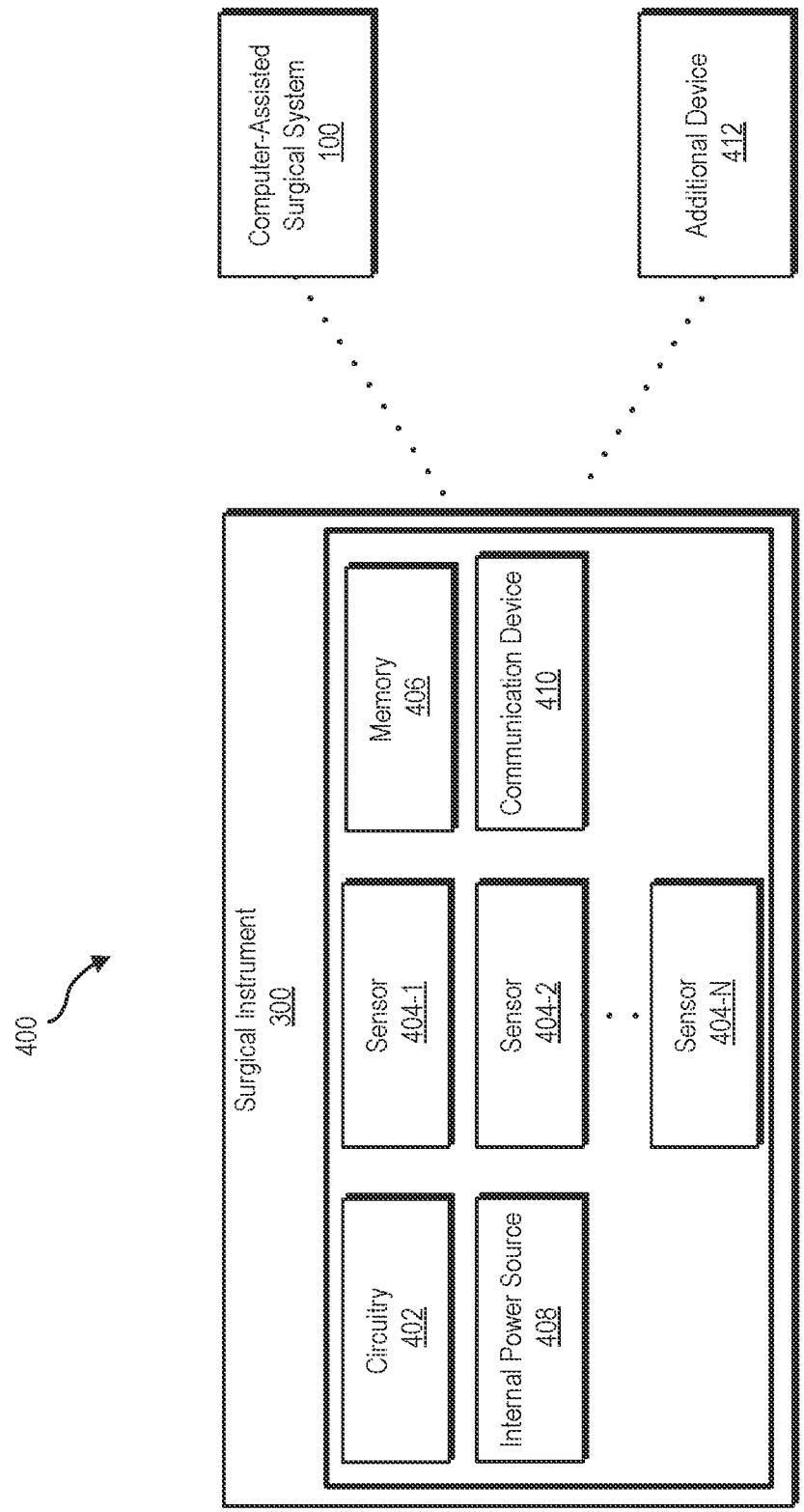
FIG. 4 illustrates an exemplary implementation of a surgical instrument according to principles described herein.

FIG. 4 shows an exemplary implementation 400 in which surgical instrument 300 may be provided. As shown in FIG. 4, surgical instrument 300 includes various components associated with the intended function of surgical instrument 300 and/or associated with detecting environmental condition information. For example, surgical instrument 300 includes circuitry 402, one or more sensors 404 (e.g., sensors 404-1 through 404-N), a memory 406, an internal power source 408, and a communication device 410 selectively and communicatively coupled to one another. Circuitry 402, sensors 404, memory 406, internal power source 408, and communication device 410 may be included as part of surgical instrument 300 in any suitable manner. For example, circuitry 402, sensors 404, memory 406, internal power source 408, and/or communication device 410 may be disposed within one or more of housing 302 and shaft portion 304 in certain implementations.

Circuitry 402 is configured to facilitate surgical instrument 300 operating according to the intended function of surgical instrument 300. For example, when surgical instrument 300 is implemented by an imaging device such as an endoscope, the intended function of surgical instrument 300 is to capture images of a surgical space during a surgical procedure. Accordingly, in such an example, circuitry 402 may include any suitable combination of wirings, processors, memories, and/or other electrical components suitable to facilitate surgical instrument 300 capturing the images of the surgical space. Circuitry 402 is configured to be powered and operate only while surgical instrument 300 is connected to an external power source. The external power source may include any suitable power source that is external to surgical instrument 300. In certain examples, an external power source may be part of system 100. For example, circuitry 402 may be configured to be powered and operate only while surgical instrument 300 is communicatively coupled to a manipulator arm (e.g., manipulator arm 112-1) and receiving power from system 100. In such examples, an external power source may correspond to one or more components of system 100 (e.g., manipulator arm 112-1 and/or auxiliary system 106). In certain alternative examples, an external power source may not be part of system 100. In certain examples, circuitry 402 may be disposed within housing 302 and/or shaft portion 304. In certain examples, circuitry 402 may be integrated as part of housing 302 and/or shaft portion 304. For example, circuitry 402 may formed within or on a wall of housing 302 or in any other suitable manner in certain implementations.

Sensors 404 may include any suitable sensor or combination of sensors that may be used to detect environmental condition information associated with surgical instrument 300. The environmental condition information detected by sensors 404 may include information regarding an environment inside of surgical instrument (e.g., inside housing 302 and/or shaft portion 304) and/or an environment outside of surgical instrument 300. Sensors 404 may include a temperature sensor, a humidity sensor, a motion sensor, a global positioning system ("GPS") sensor, and/or any other suitable sensor.

A temperature sensor may be configured to detect a temperature experienced at any given time by the surgical instrument. The temperature sensor may be configured to detect a temperature inside housing 302 and/or outside of housing 302. Any suitable temperature sensor may be used as may serve a particular implementation.

A humidity sensor may be configured to detect a humidity level associated with surgical instrument 300. In certain examples, the humidity sensor may be configured to detect a humidity level inside of housing 302. Accordingly, in such examples a humidity sensor may be provided internally within housing 302. Additionally or alternatively, a humidity sensor may be configured to detect a humidity level outside of housing 302. Any suitable humidity sensor may be used as may serve a particular implementation.

A motion sensor may be configured to detect motion (e.g., vibrations, accelerations, drop forces, impacts, etc.) experienced by surgical instrument 300. Any suitable motion sensor may be used. For example, the motion sensor may include an accelerometer, an impact monitoring sensor, and/or any other suitable sensor configured to detect movement experienced by surgical instrument 300. In certain examples, a plurality of motion sensors may be provided as part of surgical instrument 300. For example, a first motion sensor may be provided together with housing 302 to monitor whether housing 302 experiences any impact forces. A second motion sensor may be provided together in a connector portion provided on a distal end of a cord (e.g., the end that plugs into auxiliary system 106) attached to surgical instrument 300.

A GPS sensor may be configured to track a geographic location of the surgical instrument at any given time. Any suitable GPS sensor may be used as may serve a particular implementation.

In certain examples, sensors 404 may be configured to detect the environmental condition information while surgical instrument 300 is disconnected from an external power source (e.g., while disconnected from manipulator arm 112-1 and auxiliary system 106). It is understood that the environmental condition information detected by sensors 404 may not be associated with the intended function of surgical instrument 300. For example, when surgical instrument 300 corresponds to an endoscope, sensors 404 may include a temperature sensor and/or a humidity sensor, which are configured to detect information that is not associated with the intended function of an endoscope of capturing images of a surgical space.

Sensors 404 may be configured to detect the environmental condition information at any suitable time during the life cycle of surgical instrument 300. For example, sensors 404 may be configured to detect the environmental condition information during transit from a manufacturer of surgical instrument 300 to a facility (e.g., a hospital), while in inventory at a facility, during a surgical procedure, during a sterilization procedure, and/or at any other suitable time.

In certain examples, at least some of sensors 404 may be included inside of housing 302. Additionally or alternatively, one or more of sensors 404 may be provided on an exterior surface of housing 302, inside shaft portion 304, on an exterior surface of shaft portion 304, and/or in any other suitable position. In examples where surgical instrument 300 includes a cord that connects surgical instrument 300 to auxiliary system 106, one or more of sensors 404 may be provided together with a portion of the cord.

Memory 406 is configured to store the environmental condition information detected by sensors 404 while surgical instrument 300 is disconnected from an external power source. Memory 406 may include any suitable type of storage device, such as those described herein. In certain examples, memory 406 may be implemented by storage facility 204 shown in FIG. 2. In certain examples, memory 406 may be disposed within housing 302 and/or shaft portion 304.

Internal power source 408 is configured to provide operating power to sensors 404 and memory 406 while surgical instrument 300 is disconnected from an external power source (e.g., while disconnected from system 100). Internal power source 408 may include any suitable type of power source as may serve a particular implementation. In certain examples, internal power source 408 may include a rechargeable battery configured to be recharged in any suitable manner. In certain examples, internal power source 408 may be configured to be recharged while surgical instrument 300 is attached to system 100 (e.g., while attached to a manipulator arm). Additionally or alternatively, internal power source 408 may be configured to be recharged while detached from system 100 (e.g., while detached from a manipulator arm). For example, internal power source 408 may be inductively recharged by an additional device. To illustrate, a sterilization device such as an autoclave may include an inductive charging device configured to recharge internal power source 408 while surgical instrument 300 is being sterilized within the autoclave.

Additionally or alternatively, internal power source 408 may include a capacitive power supply that may be implemented in any suitable manner to provide power to surgical instrument 300.

Additionally or alternatively, internal power source 408 may include a kinetic power generator configured to convert movement of surgical instrument 300 into energy to be stored by internal power source 408. For example, as surgical instrument 300 is moved from a storage location (e.g., an inventory room) at a facility to an operating room, the kinetic power generator may covert vibrations and/or movements of surgical instrument 300, in any suitable manner, into energy used to recharge internal power source 408. In certain examples, internal power source 408 may be disposed within housing 302 and/or shaft portion 304.

As shown in FIG. 4, surgical instrument 300 may be communicatively coupled to computer-assisted surgical system 100 and/or an additional device 412. Additional device 412 may include any suitable computing device configured to communicate with communication device 410. For example, additional device 412 may be a tablet computer, a laptop computer, a smartphone, a computing device having radio-frequency identification ("RFID") reader or any other suitable device.

Communication device 410 is configured to communicate the detected environmental condition information to system 100 and/or additional device 412 communicatively coupled to surgical instrument 300. Communication device 410 may be configured to communicate the environmental condition information in any suitable manner. For example, communication device 410 may be configured to communicate the detected environmental condition information by way of a wireless connection while surgical instrument 300 is detached from a manipulator arm of system 100. Additionally or alternatively, communication device 410 may be configured to communicate the detected environmental condition information by way of a wired connection (e.g., through contact pins) while surgical instrument 300 is attached to a manipulator arm of system 100. To that end, communication device 410 may include any suitable electrical components configured to facilitate such wireless and/or wired communication. Communication device 410 may be configured to communicate the environmental condition information using any suitable wireless communication protocol (e.g., BLUETOOTH, Wi-Fi, etc.). In certain examples, communication device 410 may include an RFID tag that is configured to facilitate transmitting the environmental condition information upon receiving an interrogation signal from an RFID reader.

In certain examples, communication device 410 may be configured to encrypt environmental condition information, notifications, and/or any other information transmitted to system 100 and/or additional device 412. In such examples, communication device 410 may use any suitable encryption protocol as may serve a particular implementation.

Communication device 410 may be configured to communicate the detected environmental condition information at any suitable time. For example, communication device 410 may be configured to communicate the detected environmental condition information while surgical instrument 300 is still in manufacturer packaging, while surgical instrument 300 is connected to system 100 and is being used during a surgical procedure, while surgical instrument 300 is disconnected from system 100, and/or at any other suitable time. In certain examples, communication device may be configured to communicate the detected environmental condition information while surgical instrument 300 is subjected to a sterilization procedure. For example, communication device 410 may be configured to communicate the detected environmental condition information to an additional device while surgical instrument 300 is in an autoclave. In so doing, it may be possible to monitor environmental condition information in real time as surgical instrument 300 is subjected to a sterilization procedure. Additionally or alternatively, communication device 410 may be configured to communicate the detected environmental condition information after surgical instrument 300 is subjected to a sterilization procedure.

Returning to FIG. 2, detection system 200 may be configured to instruct sensors 404 to detect environmental condition information at any suitable time and in any suitable manner. In certain examples, detection system 200 may direct a first type of sensor included in sensors 404 to continually monitor for environmental condition information and may direct a second type of sensor included in sensors 404 to periodically monitor for environmental condition information. For example, detection system 200 may instruct a motion sensor included as part of surgical instrument 300 to continually check for impact forces experienced by surgical instrument 300. On the other hand, detection system 200 may instruct a temperature sensor included as part of surgical instrument 300 to periodically detect a temperature associated with surgical instrument 300 (e.g., every five minutes). In so doing, it may be possible to avoid unnecessarily using energy stored by internal power source 408.

Detection system 200 may be configured to direct memory 406 to store environmental condition information in any suitable manner and at any suitable time. In certain examples, detection system 200 may be configured to direct memory 406 to store all of the environmental condition information detected by sensors 404. In certain alternative examples, detection system 200 may be configured to direct memory 406 to store environmental condition information only when the environmental condition information is above a predefined threshold. For example, detection system 200 may direct memory 406 to store information associated with the humidity inside housing 302 only when the detected humidity level is above a predefined level. In another example, detection system 200 may direct memory 406 to store information detected by a motion sensor only when an impact force detected by the motion sensor is above a predefined level. In so doing, it may be possible to conserve storage space associated with memory 406. In certain alternative examples, detection system 200 may be configured to direct memory 406 to store environmental condition information only when the environmental condition information is below a predefined threshold.

Additionally or alternatively, detection system 200 may direct memory 406 to store environmental condition information only when the environmental condition information is above a predefined threshold for at least a predetermined amount of time. For example, detection system 200 may direct memory 406 to store information associated with the temperature of surgical instrument 300 only when the temperature exceeds a predefined temperature for a predetermined amount of time (e.g., five minutes).

In certain examples, detection system 200 may direct memory 406 to automatically delete environmental condition information from memory 406 after the environmental condition information is communicated to another device (e.g., system 100 and/or additional device 412).

Detection system 200 may determine, based on the environmental condition information, an operational condition of surgical instrument. For example, the determined operational condition of the surgical instrument may correspond to a fully operational condition, a partially operational condition, or a non-operational condition. When detection system 200 determines that surgical instrument 300 is in a fully operational condition, surgical instrument 300 has not been subjected to any condition or event that would prevent surgical instrument 300 from operating properly. When detection system 200 determines that surgical instrument 300 is in a partially operational condition, surgical instrument 300 may have been subjected to one or more conditions that do not prevent operation of surgical instrument 300 but nonetheless may prevent surgical instrument from operating as effectively or efficiently. For example, if surgical instrument 300 is an endoscope, moisture within housing 302 may reduce image quality of images captured by the endoscope. When detection system 200 determines that surgical instrument 300 is in a non-operational condition, surgical instrument 300 may have been subjected to some condition or event resulting in operational failure of surgical instrument 300. For example, surgical instrument 300 may have been dropped so as to break a key component of surgical instrument 300 such that surgical instrument 300 is no longer capable of, for example, capturing images. The operational condition of a surgical instrument may be considered as "faulty" when the surgical instrument has a partially operational condition or a non-operational condition.

In certain examples, detection system 200 may be configured to disable operation of surgical instrument 300 based on the determined operational condition of surgical instrument 300. For example, detection system 200 may determine that surgical instrument 300 is in a partially operational condition that may result in surgical instrument 300 failing to operate correctly and that could potentially result in unsafe conditions during a surgical procedure. Accordingly, detection system 200 may disable surgical instrument 300, in any suitable manner, to prevent surgical instrument 300 from being usable while communicatively coupled to system 100. After surgical instrument 300 is processed such that surgical instrument 300 is in a fully operational condition, detection system 200 may enable operation of surgical instrument 300 in any suitable manner. For example, surgical instrument 300 may be disabled by detection system 200 based on a humidity level within housing 302 being above a predefined threshold. Surgical instrument 300 may then be subjected to a dry cycle that lowers the humidity level within housing 302. Based on the changed humidity level, detection system 200 may determine that surgical instrument 300 is fully operational and may enable operation of surgical instrument 300.

In certain examples, detection system 200 may be configured to provide a notification indicating the determined operational condition. Such a notification may be provided in any suitable manner. In certain examples, detection system 200 may provide the notification to a user by way of a display screen of an additional device (e.g., additional device 412) communicatively coupled to surgical instrument 300. Additionally or alternatively, while surgical instrument 300 is communicatively connected to system 100, detection system 200 may provide the notification for display to a user by way of user control console 104 and/or display monitor 114.

The notification provided by detection system 200 may include any suitable information as may serve a particular implementation. For example, the notification may identify when the environmental condition information was detected, where the environmental condition information was detected, how many times the environmental condition information was detected, etc. In certain examples, the determined operational condition indicated by the notification may indicate that surgical instrument 300 is faulty and needs to be replaced by an additional surgical instrument. In examples where detection system 200 has disabled surgical instrument 300, the notification may indicate such to a user and include any other information that may be helpful to facilitate processing surgical instrument 300 so that surgical instrument 300 is no longer disabled. Alternatively, the notification may include information to facilitate exchanging surgical instrument 300 for an additional surgical instrument that is not disabled.

In addition, the notification provided by detection system 200 may be provided at any suitable time and while surgical instrument 300 is at any suitable location. For example, the notification may be provided at any suitable time while surgical instrument 300 is in an operating room, in a storage room, in a transit vehicle on the way for delivery to a facility such as a hospital, and/or at any other suitable location.

Figure 5:
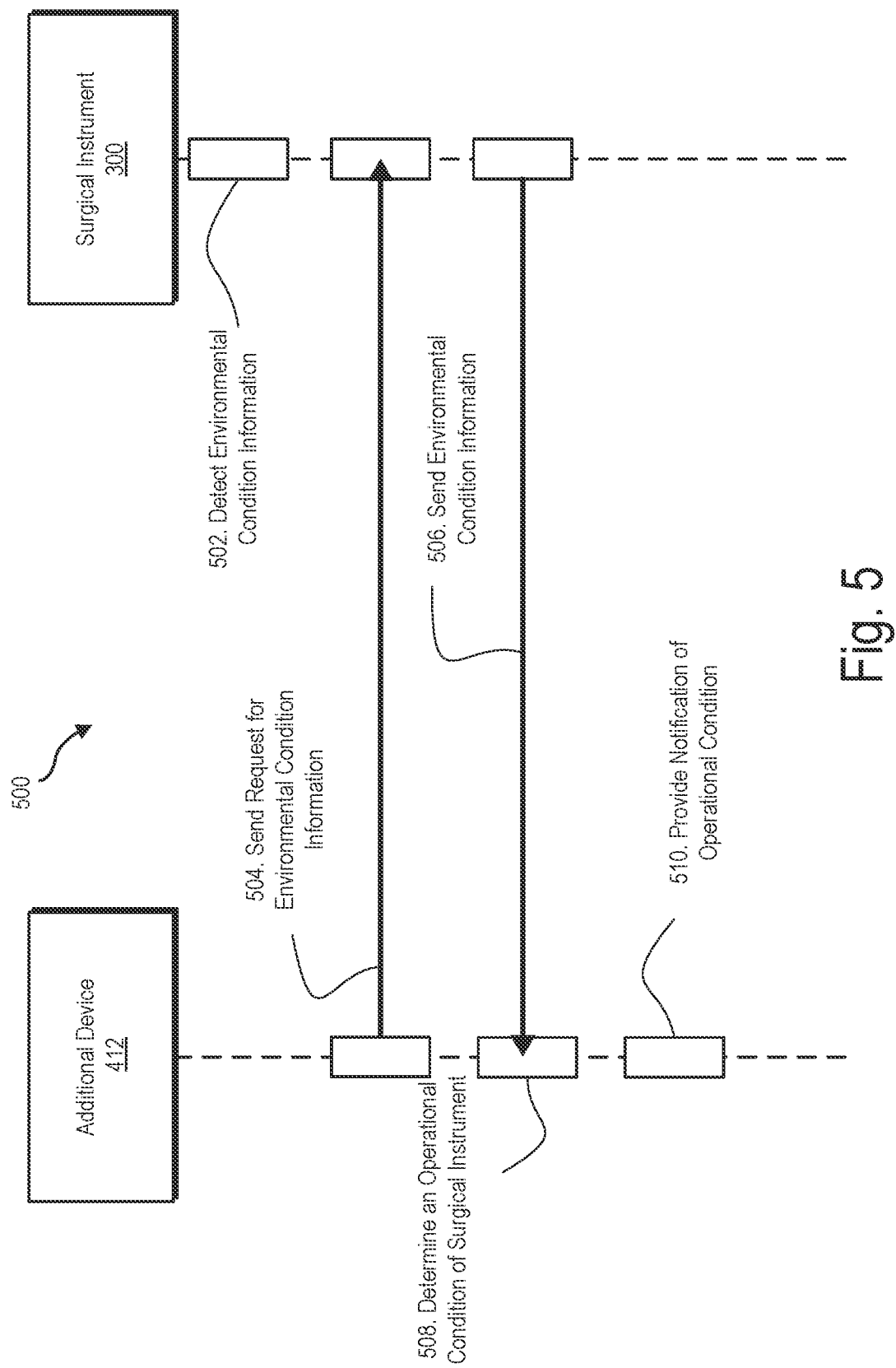
FIGS. 5-6 illustrate exemplary sequence diagrams according to principles described herein.

FIG. 5 illustrates an exemplary sequence diagram 500 showing communications that may occur between surgical instrument 300 and additional device 412 in certain implementations. As shown in FIG. 5, surgical instrument 300 detects environmental condition information in operation 502. Additional device 412 sends a request for environmental condition information in operation 504. In response to the request, surgical instrument 300 sends the environmental condition information, in any suitable manner, to additional device 412 in operation 506. In operation 508, additional device 412 determines an operational condition of surgical instrument 300. In operation 510, additional device 412 provides a notification of the operational condition of surgical instrument 300. For example, additional device 412 may determine, based on the environmental condition information, that surgical instrument 300 was not subjected to sufficient temperature for a sufficient amount of time during a sterilization procedure. In such an example, additional device 412 may provide a notification to a user (e.g., by way of a display screen associated with additional device 412) indicating, for example, that surgical instrument 300 was not sterilized properly.

Figure 6:
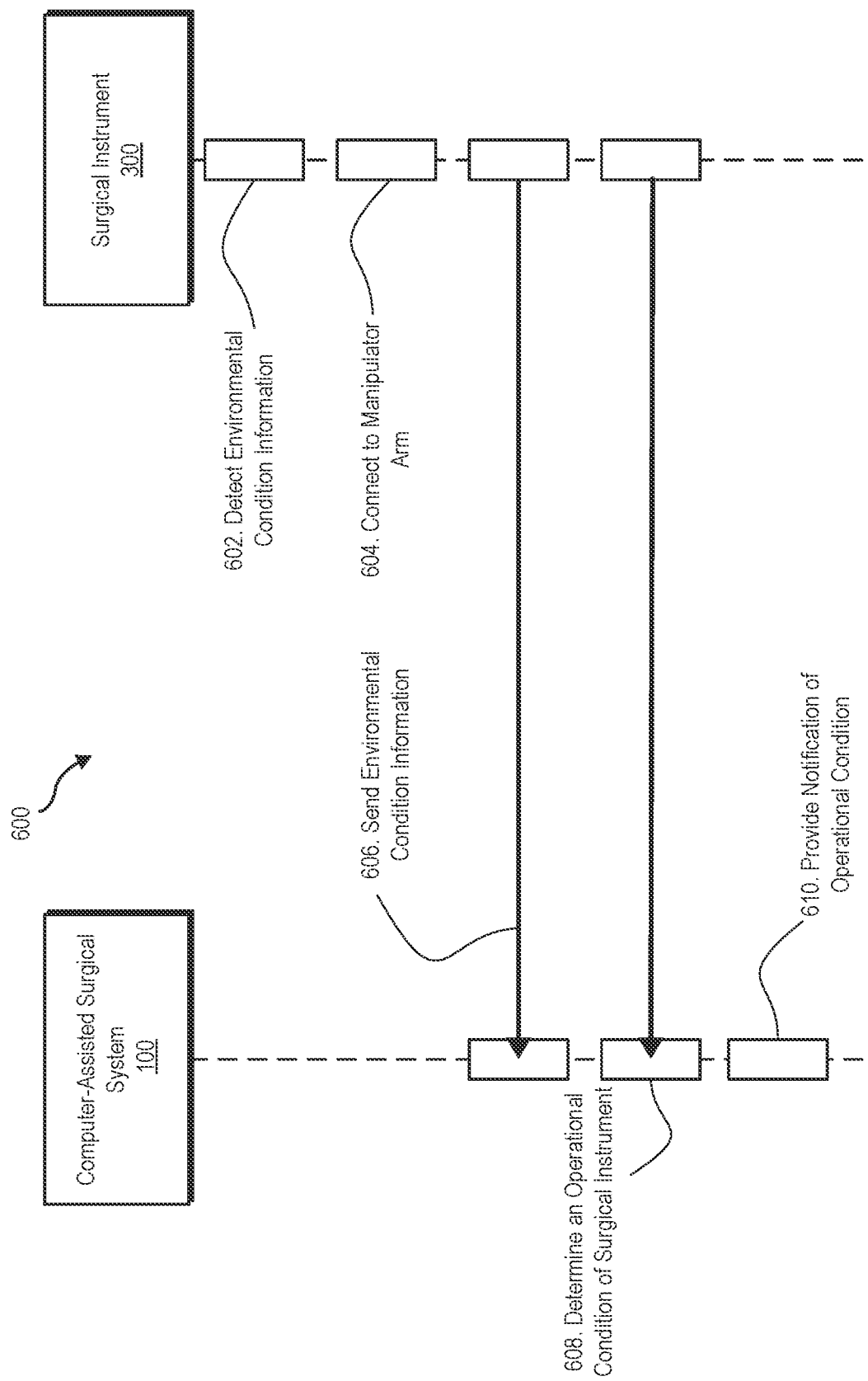

FIG. 6 illustrates an exemplary sequence diagram 600 showing communications that may occur between surgical instrument 300 and computer-assisted surgical system 100 in certain implementations. As shown in FIG. 6, surgical instrument 300 detects environmental condition information in operation 602. Subsequent to detecting the environmental condition information, surgical instrument 300 may be communicatively connected to a manipulator arm of system 100 (and/or any other suitable part of system 100) in operation 604. In operation 606, surgical instrument 300 may send the environmental condition information to system 100. As described herein, while surgical instrument is communicatively connected to the manipulator arm, the environmental condition information may be sent to system 100 by way of a wired communication interface. In operation 608, system 100 may determine, based on the environmental condition information, an operational condition of surgical instrument 300. In operation 610, system 100 may provide a notification of the operational condition of surgical instrument 300. To illustrate an example, system 100 may determine, based on the environmental condition information, that a humidity level within housing 302 of surgical instrument 300 is above a predefined level. Based on the humidity level, system 100 may determine that surgical instrument 300 has not been dried properly and, as a result, may not function properly during a surgical procedure. Accordingly, system 100 may provide a notification (e.g., through a display device associated with user control console 104 and/or any other suitable display associated with system 100) indicating that surgical instrument is not in condition for use.

Figure 7:
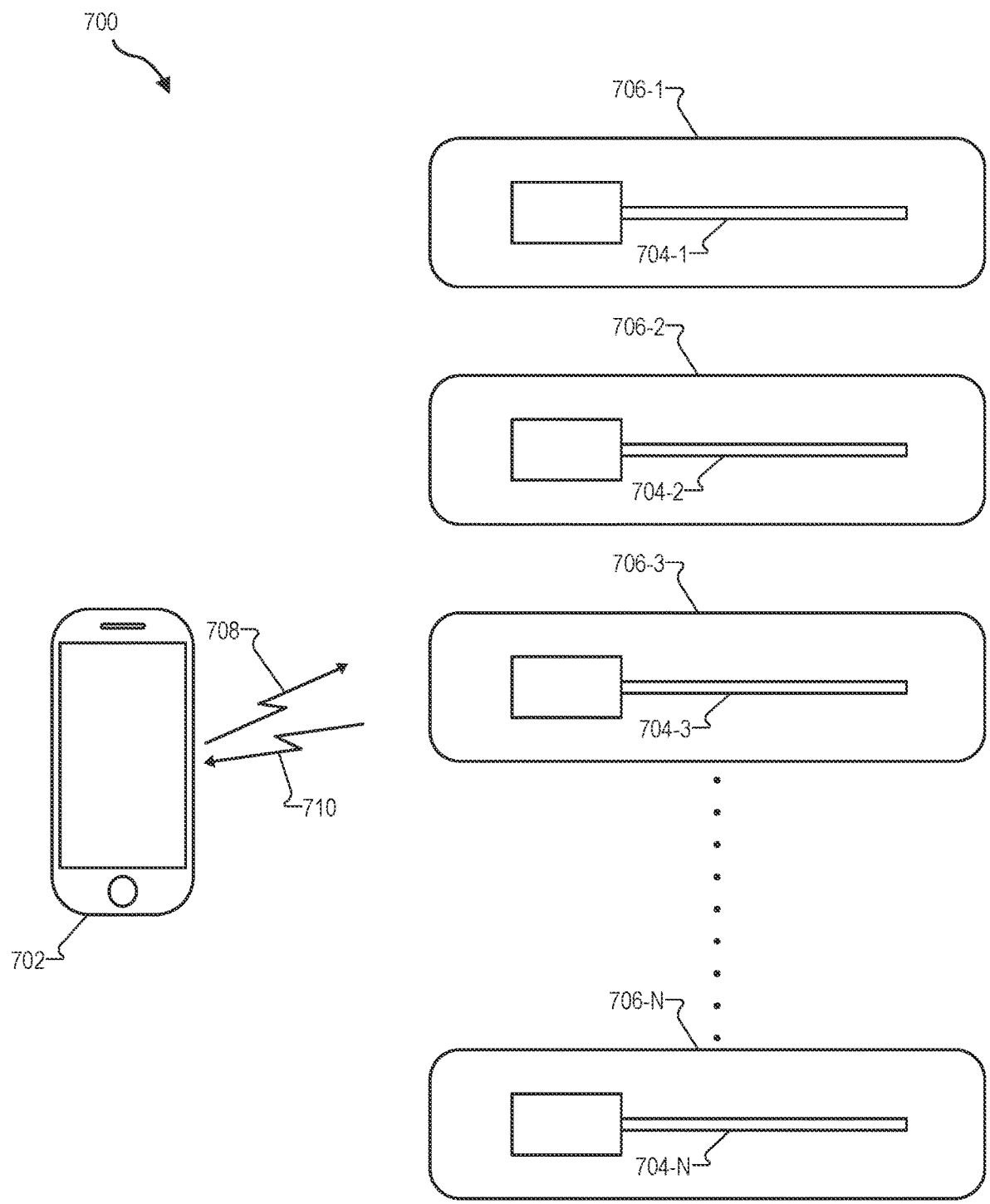
FIG. 7 illustrates another exemplary implementation of a surgical instrument condition detection system according to principles described herein.

FIG. 7 illustrates an exemplary implementation 700 that may be used in certain examples to wirelessly receive environmental condition information from surgical instruments prior to the surgical instruments being used in a surgical procedure. As shown in FIG. 7, implementation 700 shows a mobile computing device 702 that is configured to wirelessly communicate, in any suitable manner, with a plurality of surgical instruments 704 (e.g., surgical instruments 704-1 through 704-N) while surgical instruments 704 are provided within packaging 706 (e.g., packaging 706-1 through 706-N). In certain examples, packaging 706 may correspond to packaging provided by a manufacturer of surgical instruments 704. Mobile computing device 702 may communicate with surgical instruments 704 in any suitable manner using any suitable wireless communication protocol, such as those described herein. For example, mobile computing device 702 may include an RFID reader. When mobile computing device 702 is within a predefined range of, for example, surgical instrument 704-3, mobile computing device 702 may provide an RFID interrogation signal 708 to surgical instrument 704-3 to request environmental condition information from surgical instrument 704-3. In response to RFID interrogation signal 708, surgical instrument 704-3 may transmit the environmental condition information in a response signal 710 to mobile computing device 702.

In certain examples, each of packaging 706 may include an additional power source (e.g. a battery) (not shown) configured to power one or more of the sensors of surgical instruments 704 while surgical instruments 704 are stored within packaging 706.

In certain examples, surgical instruments such as those described herein may include one or more indicators configured to provide a user with a notification regarding detected environmental condition information. Such indicators may be provided together with a surgical instrument in any suitable manner. In certain examples, an indicator may be externally viewable from an external surface of a surgical instrument. To illustrate, FIGS. 8A and 8B show an exemplary configuration 800 in which an indicator 802 is provided on an external surface of a housing 804 of an endoscope. Indicator 802 includes a window portion 806 that is configured to be closed initially, as shown in FIG. 8A. When the detected environmental condition information reaches some predefined level, window portion 806 is configured to slide in the direction of arrow 808 to reveal a notification 810, as shown in FIG. 8B. To illustrate an example, a humidity sensor provided within housing 804 may detect that the humidity within housing 804 is above an acceptable level for the endoscope to operate properly. In response to the detected humidity, the endoscope may energize a solenoid in any suitable manner to open window portion 806 and expose notification 810, as shown in FIG. 8B. In this example, notification 810 is configured to notify a user that the endoscope is not sufficiently dry. In response to notification 810, a user may then cause the endoscope may undergo a drying procedure to reduce the humidity level. After the endoscope is subjected to the drying procedure, window portion 806 may automatically close so as to return to the position shown in FIG. 8A. The exemplary indicator shown in FIGS. 8A and 8B is provided for illustrative purposes only. It is understood that other types of indicators may be used in other implementations. For example, instead of an indicator that includes a solenoid actuated window portion, other implementations may include an externally viewable light-emitting diode ("LED") that lights up when the detected environmental condition information satisfies some predefined requirement.

In certain examples, detection system 200 may utilize detected environmental condition information associated with a surgical instrument to provide feedback, training, and/or any suitable information regarding proper use and/or care of a surgical instrument. For example, detection system 200 may determine based on detected environmental condition information that surgical instruments used at a particular facility (e.g., hospital) typically have a moisture level after sterilization that that is above a predefined threshold. Based on such a determination, detection system 200 may provide, in any suitable manner, a notification instructing users at the facility to increase the time of a dry cycle when sterilizing the surgical instruments. In another example, detection system 200 may determine based on detected environmental condition information, that surgical instruments at a particular facility typically achieve a desired temperature during sterilization, but the desired temperature is often not maintained for a sufficient amount of time. Based on such a determination, detection system 200 may provide a notification instructing users at the facility to increase the amount of time that the surgical instruments are heated during sterilization.

In certain examples, detection system 200 may utilize environmental condition information and/or any other suitable information associated with surgical instruments such as those described herein to manage and/or track inventory at a facility. For example, detection system 200 may utilize environmental condition information associated with surgical instruments to monitor geographic locations of surgical instruments in inventory, conditions of surgical instruments while in inventory, an amount of time that surgical instruments have been in inventory, and/or any other suitable information associated with the surgical instruments. In such examples, detection system 200 may wirelessly receive such information from the surgical instruments in any suitable manner. For example, detection system 200 may receive such information by way of an RFID tag provided with each surgical instrument in inventory.

Figure 9:
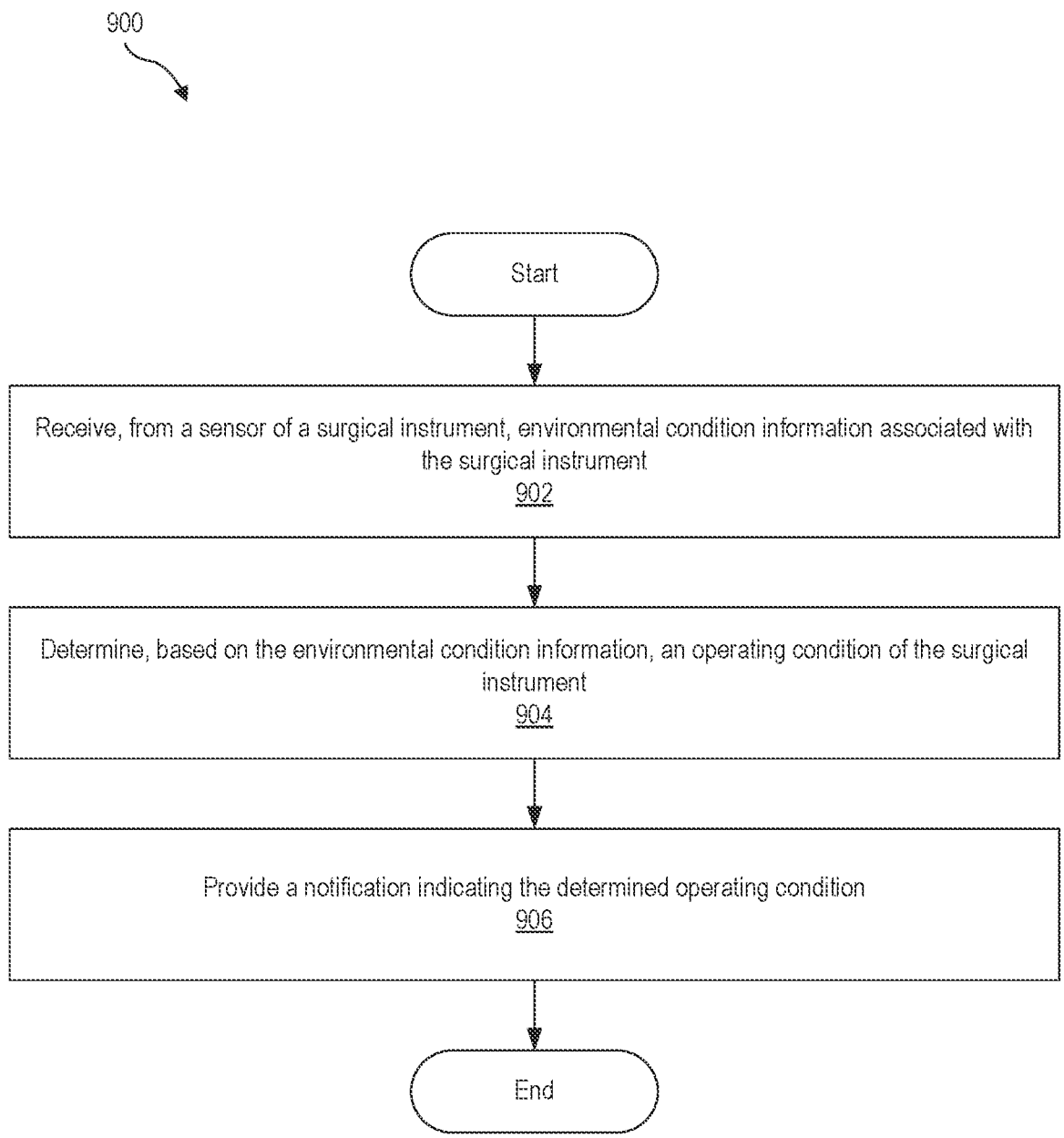
FIGS. 9-10 illustrate exemplary methods for determining condition information of a surgical instrument according to principles described herein.

FIG. 9 illustrates an exemplary method for determining condition information of a surgical instrument. While FIG. 9 illustrates exemplary operations according to one embodiment, other embodiments may omit, add to, reorder, and/or modify any of the operations shown in FIG. 9. One or more of the operations shown in FIG. 9 may be performed by a system such as surgical instrument detection system 200, any components included therein, and/or any implementation thereof.

In operation 902, a system (e.g., surgical instrument condition detection system 200) may receive, from a sensor of a surgical instrument, environmental condition information associated with the surgical instrument. As described herein, the environmental condition information may be detected by the sensor while the sensor uses operating power from an internal power source of the surgical instrument and while the surgical instrument is disconnected from an external power source (e.g., while disconnected from computer-assisted surgical system 100). In certain examples, the environmental condition information may be detected by the sensor while the sensor uses operating power from an internal power source disposed within the surgical instrument. The surgical instrument includes circuitry configured to be powered and operate only while the surgical instrument is connected to the external power source. Operation 902 may be performed in any of the ways described herein.

In operation 904, the system may determine, based on the environmental condition information, an operational condition of the surgical instrument. Operation 904 may be performed in any of the ways described herein.

In operation 906, the system may provide a notification indicating the determined operational condition. In certain examples, the notification may be transmitted in any suitable manner to an additional device communicatively coupled to the surgical instrument. Operation 906 may be performed in any of the ways described herein.

Figure 10:
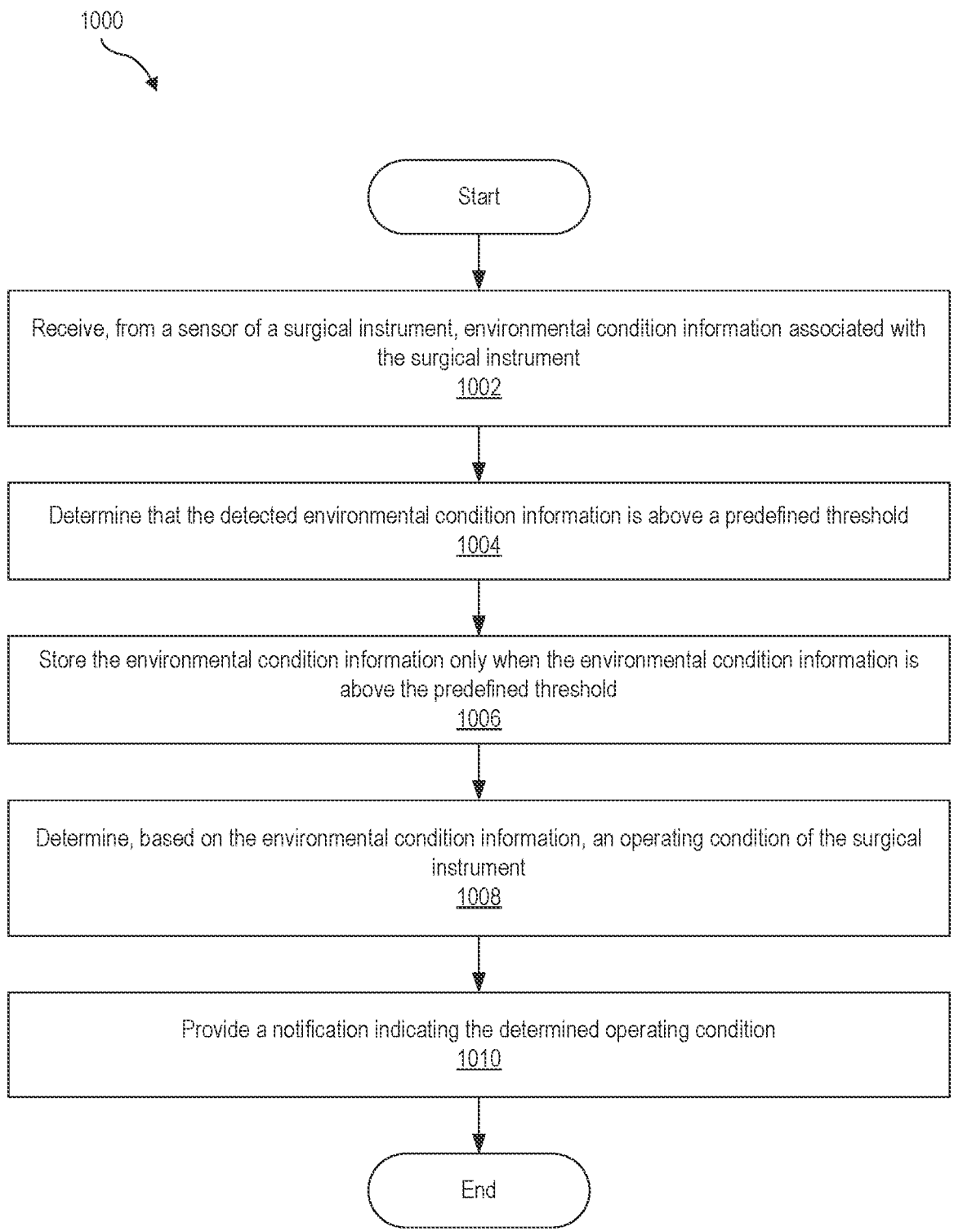

FIG. 10 illustrates another exemplary method for determining condition information of a surgical instrument. While FIG. 10 illustrates exemplary operations according to one embodiment, other embodiments may omit, add to, reorder, and/or modify any of the operations shown in FIG. 10. One or more of the operations shown in FIG. 10 may be performed by a system such as surgical instrument detection system 200, any components included therein, and/or any implementation thereof.

In operation 1002, a system (e.g., surgical instrument condition detection system 200) may receive, from a sensor of a surgical instrument, environmental condition information associated with the surgical instrument. As described herein, the environmental condition information may be detected by the sensor while the sensor uses operating power from an internal power source of the surgical instrument and while the surgical instrument is disconnected from an external power source (e.g., while disconnected from computer-assisted surgical system 100). The surgical instrument includes circuitry configured to be powered and operate only while the surgical instrument is connected to the external power source. Operation 1002 may be performed in any of the ways described herein.

In operation 1004, the system may determine that the environmental condition information is above a predefined threshold. Operation 1004 may be performed in any of the ways described herein.

In operation 1006, the system may store the environmental condition information only when the environmental condition information is above the predefined threshold. Operation 1006 may be performed in any of the ways described herein.

In operation 1008, the system may determine, based on the environmental condition information, an operational condition of the surgical instrument. Operation 1008 may be performed in any of the ways described herein.

In operation 1010, the system may provide a notification indicating the determined operational condition. In certain examples, the notification may be transmitted in any suitable manner to an additional device communicatively coupled to the surgical instrument. Operation 1010 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 11:
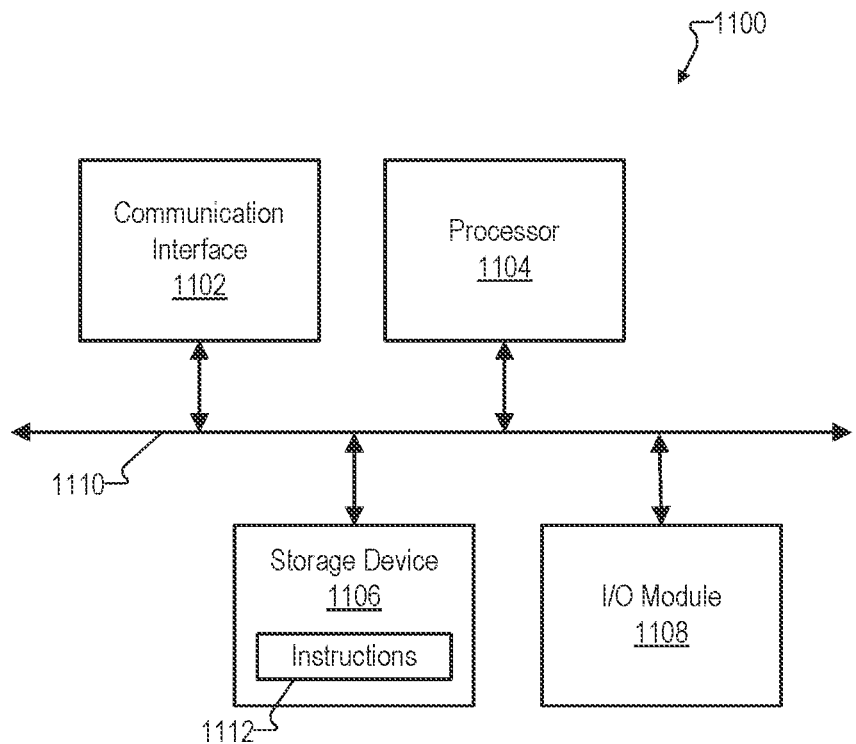
FIG. 11 illustrates an exemplary computing device according to principles described herein.

FIG. 11 illustrates an exemplary computing device 1100 that may be specifically configured to perform one or more of the processes described herein. As shown in FIG. 11, computing device 1100 may include a communication interface 1102, a processor 1104, a storage device 1106, and an input/output ("I/O") module 1108 communicatively connected one to another via a communication infrastructure 1110. While an exemplary computing device 1100 is shown in FIG. 11, the components illustrated in FIG. 11 are not intended to be limiting. Additional or alternative components may be used in other embodiments. Components of computing device 1100 shown in FIG. 11 will now be described in additional detail.

Communication interface 1102 may be configured to communicate with one or more computing devices. Examples of communication interface 1102 include, without limitation, a wired network interface (such as a network interface card), a wireless network interface (such as a wireless network interface card), a modem, an audio/video connection, and any other suitable interface.

Processor 1104 generally represents any type or form of processing unit capable of processing data and/or interpreting, executing, and/or directing execution of one or more of the instructions, processes, and/or operations described herein. Processor 1104 may perform operations by executing computer-executable instructions 1112 (e.g., an application, software, code, and/or other executable data instance) stored in storage device 1106.

Storage device 1106 may include one or more data storage media, devices, or configurations and may employ any type, form, and combination of data storage media and/or device. For example, storage device 1106 may include, but is not limited to, any combination of the non-volatile media and/or volatile media described herein. Electronic data, including data described herein, may be temporarily and/or permanently stored in storage device 1106. For example, data representative of computer-executable instructions 1112 configured to direct processor 1104 to perform any of the operations described herein may be stored within storage device 1106. In some examples, data may be arranged in one or more databases residing within storage device 1106.

I/O module 1108 may include one or more I/O modules configured to receive user input and provide user output. One or more I/O modules may be used to receive input for a single virtual experience. I/O module 1108 may include any hardware, firmware, software, or combination thereof supportive of input and output capabilities. For example, I/O module 1108 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1108 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1108 is configured to provide graphical data to a display for presentation to a user. The graphical data may be representative of one or more graphical user interfaces and/or any other graphical content as may serve a particular implementation.

In some examples, any of the systems, computing devices, and/or other components described herein may be implemented by computing device 1100. For example, storage facility 204 and/or memory 406 may be implemented by storage device 1106, and processing facility 202 may be implemented by processor 1104.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A surgical instrument comprising:
   circuitry configured to control operation of the surgical instrument, the circuitry configured to be powered and operate only while the surgical instrument is connected to an external power source that is part of a computer-assisted surgical system; and
   a wireless communication device configured to wirelessly communicate environmental condition information detected by a sensor to an additional device communicatively coupled to the surgical instrument,
   wherein the wireless communication device is configured to wirelessly communicate the detected environmental condition information prior to the surgical instrument being removed from packaging provided by a manufacturer of the surgical instrument.

2. The surgical instrument of claim 1, further comprising:
   a memory configured to store the environmental condition information; and
   an internal power source within the surgical instrument and configured to provide operating power to the sensor and the memory while the surgical instrument is disconnected from the external power source.

3. The surgical instrument of claim 1, further comprising a memory configured to store the environmental condition information, wherein the memory is further configured to store the detected environmental condition information at least one of:
   prior to the surgical instrument being removed from the packaging provided by the manufacturer of the surgical instrument; or
   while a sterilization procedure is being performed on the surgical instrument.

4. The surgical instrument of claim 1, wherein the sensor is configured to detect the environmental condition information while the surgical instrument is disconnected from the external power source.

5. The surgical instrument of claim 1, further comprising a wired communication device that is configured to communicate the detected environmental condition information by way of a wired connection while the surgical instrument is attached to the computer-assisted surgical system.

6. The surgical instrument of claim 1, wherein the wireless communication device is configured to wirelessly communicate the detected environmental condition information while a sterilization procedure is being performed on the surgical instrument.

7. The surgical instrument of claim 1, wherein the sensor is further configured to detect the environmental condition information while the surgical instrument is connected to the external power source.

8. The surgical instrument of claim 1, further comprising a memory configured to store the environmental condition information,
   wherein the storing of the detected environmental condition information in the memory is performed in response to the detected environmental condition information exceeding a predefined threshold.

9. The surgical instrument of claim 1, further comprising an indicator provided on an external surface of the surgical instrument, the indicator configured to provide a user with a notification associated with the detected environmental condition information.

10. The surgical instrument of claim 1, wherein the environmental condition information indicates that the surgical instrument is faulty.

11. The surgical instrument of claim 1, wherein the detected environmental condition information includes information regarding an environment inside the surgical instrument.

12. The surgical instrument of claim 1, wherein the sensor includes one or more of
    a temperature sensor configured to detect a temperature experienced by the surgical instrument,
    a humidity sensor configured to detect a humidity level associated with the surgical instrument,
    a motion sensor configured to detect motion experienced by the surgical instrument, and
    a global positioning system ("GPS") sensor.

13. The surgical instrument of claim 1, further comprising:
    a memory configured to store the environmental condition information;
    a housing; and
    a shaft portion coupled to the housing,
    wherein the circuitry, the sensor, and the memory are disposed within one or more of the housing or the shaft portion.

14. A system comprising:
    a memory storing instructions; and a processor communicatively coupled to the memory and configured to execute the instructions to:
receive, from a sensor of a surgical instrument, environmental condition information associated with the surgical instrument and detected by the sensor while the surgical instrument is disconnected from an external power source that is part of a computer-assisted surgical system, the surgical instrument including circuitry configured to control operation of the surgical instrument, the circuitry configured to be powered and operate only while the surgical instrument is connected to the external power source;
determine, based on the environmental condition information, an operational condition of the surgical instrument;
provide a notification indicating the determined operational condition of the surgical instrument; and
wirelessly communicate, to an additional device communicatively coupled to the surgical instrument, the detected environmental condition information prior to the surgical instrument being removed from packaging provided by a manufacturer of the surgical instrument.

15. The system of claim 14, wherein the processor is configured to receive the environmental condition information while the sensor uses operating power from an internal power source within the surgical instrument.

16. A method comprising:
receiving, by an instrument condition detection system from a sensor of a surgical instrument, environmental condition information associated with the surgical instrument and detected by the sensor while the surgical instrument is disconnected from an external power source that is part of a computer-assisted surgical system, the surgical instrument including circuitry configured control operation of the surgical instrument, the circuitry configured to be powered and operate only while the surgical instrument is connected to the external power source;
wirelessly transmitting, by the instrument condition detection system and to an additional device communicatively coupled to the surgical instrument, the environmental condition information prior to the surgical instrument being removed from packaging provided by a manufacturer of the surgical instrument;
determining, by the instrument condition detection system based on the environmental condition information, an operational condition of the surgical instrument; and
providing, by the instrument condition detection system, a notification indicating the determined operational condition.

17. The method of claim 16, further comprising:
determining, by the instrument condition detection system, that the detected environmental condition information is above a predefined threshold; and
storing, by the instrument condition detection system and in a memory, the environmental condition information only when the environmental condition information is above the predefined threshold.

* * * * *